US008399518B2

(12) United States Patent
Morkin et al.

(10) Patent No.: US 8,399,518 B2
(45) Date of Patent: *Mar. 19, 2013

(54) ADMINISTRATION OF 3,5-DIIODOTHYROPROPIONIC ACID FOR STIMULATING WEIGHT LOSS, AND/OR LOWERING TRIGLYCERIDE LEVELS, AND/OR TREATMENT OF METABOLIC SYNDROME

(75) Inventors: Eugene Morkin, Tucson, AZ (US); Louis R. Bucalo, Miami, FL (US); Steven Goldman, Tucson, AZ (US)

(73) Assignees: University of Arizona Office of Technology Transfer, Tucson, AZ (US); The United States of America as Represented by the Department of Veterans Affairs, Washington, DC (US)

( * ) Notice: Subject to any disclaimer, the term of this patent is extended or adjusted under 35 U.S.C. 154(b) by 463 days.

This patent is subject to a terminal disclaimer.

(21) Appl. No.: 12/596,818

(22) PCT Filed: Feb. 27, 2008

(86) PCT No.: PCT/US2008/002680
§ 371 (c)(1),
(2), (4) Date: May 28, 2010

(87) PCT Pub. No.: WO2008/106213
PCT Pub. Date: Sep. 4, 2008

(65) Prior Publication Data
US 2010/0249235 A1    Sep. 30, 2010

Related U.S. Application Data

(60) Provisional application No. 60/903,994, filed on Feb. 27, 2007.

(51) Int. Cl.
*A61K 31/19* (2006.01)
*C07C 65/00* (2006.01)
*C07C 229/00* (2006.01)

(52) U.S. Cl. ........ 514/568; 514/557; 562/405; 562/447; 562/472

(58) Field of Classification Search .................. 514/568, 514/557; 562/405, 447, 472
See application file for complete search history.

(56) References Cited

U.S. PATENT DOCUMENTS

| | | | |
|---|---|---|---|
| 3,109,023 | A | 10/1963 | Weil et al. |
| 4,451,465 | A | 5/1984 | White et al. |
| 4,772,631 | A | 9/1988 | Holloway et al. |
| 4,977,148 | A | 12/1990 | Holloway et al. |
| 4,999,377 | A | 3/1991 | Caulkett et al. |
| 5,284,971 | A | 2/1994 | Walker et al. |
| 5,883,294 | A | 3/1999 | Scanlan et al. |
| 6,534,676 | B2 | 3/2003 | Morkin et al. |
| 6,951,844 | B2 | 10/2005 | Hangeland |

FOREIGN PATENT DOCUMENTS

| | | |
|---|---|---|
| WO | WO 00/39077 | 7/2000 |
| WO | WO 2005/009433 | 2/2005 |
| WO | WO 2005/097102 | 10/2005 |

OTHER PUBLICATIONS

Huang et al. (Diabetes Care, 27(12); 2004; 3000-3001).*
Keller et al. (American Journal of Critical Care (2003) 12(2) 167-170).*
Ford et al., "Prevalence of the Metabolic Syndrome Among US Adults," *JAMA*, 287(3), pp. 356-359, Jan. 16, 2002.

* cited by examiner

*Primary Examiner* — Shirley V Gembeh
(74) *Attorney, Agent, or Firm* — Klarquist Sparkman, LLP

(57) ABSTRACT

Methods and compositions are disclosed for stimulating weight loss and/or lowering triglyceride levels in an individual mammal in need thereof. In an exemplary method, a pharmaceutical composition comprising a therapeutically effective amount of DITPA, and optionally one or more lipid-reducing agents, is administered to an individual mammal to stimulate weight loss, and/or reduce levels of triglyceride and/or lipoprotein in the mammal.

26 Claims, No Drawings

ADMINISTRATION OF 3,5-DIIODOTHYROPROPIONIC ACID FOR STIMULATING WEIGHT LOSS, AND/OR LOWERING TRIGLYCERIDE LEVELS, AND/OR TREATMENT OF METABOLIC SYNDROME

CROSS-REFERENCE TO RELATED APPLICATIONS

This application claims priority to and the benefit, under 35 U.S.C. §119(e), of U.S. Provisional Application Ser. No. 60/903,994, filed Feb. 27, 2007, and to corresponding PCT Application No. PCT/US2008/002680, designating the United States, the contents of which are incorporated herein by reference in their respective entireties.

FIELD OF THE INVENTION

This application relates to 3,5-diiodothyropropionic acid (DITPA) compositions and methods of use of such compositions for stimulating weight loss, lowering triglyceride levels, and/or treating metabolic syndrome.

BACKGROUND OF THE INVENTION

Researchers at the Centers for Disease Control and Prevention (CDC) estimated that as many as 47 million Americans may exhibit a cluster of medical conditions ("metabolic syndrome") characterized by abdominal obesity, hypertriglyceridemia, low high-density lipoprotein (HDL) cholesterol, high blood pressure, and elevated fasting blood glucose. Having three or more traits of metabolic syndrome significantly increases the risk of dying from coronary heart disease or cardiovascular disease. It has also been reported that patients with even one or two metabolic syndrome traits, or those with metabolic syndrome but without diabetes also were at increased risk for death from coronary heart disease or cardiovascular disease.

Obesity and atherosclerosis have a major impact on morbidity and mortality in the United States and many other countries. Elevated cholesterol, particularly low-density lipoprotein (LDL) cholesterol, is a major risk factor for atherosclerosis. Thyroid hormone replacement in hypothyroid individuals reduces total cholesterol and LDL-cholesterol. An excess of thyroid hormone in thyrotoxicosis causes weight loss. The weight loss consists not only of fat but also muscle mass and even myopathy can be observed.

The ability of thyroid hormone to lower cholesterol when given to hypothyroid individuals prompted efforts to design analogs that take advantage of these properties in the treatment of hypercholesterolemia. This action is the result of an accelerated LDL-cholesterol clearance rate. Triiodothyronine increases levels of both the hepatic LDL receptor and its mRNA. Additional thyroid hormone actions on lipid metabolism include increasing the activity of lipoprotein lipase.

Numerous studies have been carried out to synthesize thyroid hormone analogs that mimic the actions of the natural hormones. The objective of most of these efforts has been to develop thyromimetics that lower plasma cholesterol without adverse cardiac effects. A series of thyroxine analogs and methods of synthesis are described in U.S. Pat. No. 3,109,023. Thyroid hormone agonists that are highly selective for the thyroid hormone receptor (TR) β-subtype are described in U.S. Pat. No. 5,883,294 and WO 00/39077. U.S. Pat. No. 5,284,971 describes a class of thyromimetics, which have the distinguishing characteristic of a sulfonyl bridge in the diphenyl core. U.S. Pat. No. 6,534,676 describes a thyroid hormone analog 3,5-diiodothyropropionic acid ("DITPA") for treating patients with congestive heart failure.

The usual method employed in treating obesity has been reduction of caloric intake either by reduced caloric diet or appetite suppression. An alternative method is to stimulate metabolic rate in adipose tissue. Adipose tissue is the largest storehouse of energy in the body (in the form of triglycerides) and typically makes up 15-20% or more of the body weight in men and 20-25% more of the body weight in women. U.S. Pat. Nos. 4,451,465, 4,772,631, 4,977,148 and 4,999,377 disclose compounds possessing thermogenic properties at dosages causing few or no deleterious side-effects, such as cardiac stimulation. Goglia and Lanni in WO2005009433 describe the use of a breakdown product of thyroid hormone (3,5-diiodothyronine) as a regulator of lipid metabolism to stimulate burning of fatty acid in mitochondria.

There is a need in the art for improved methods and compositions for stimulating weight loss and lowering triglyceride levels in overweight individuals, including those with metabolic syndrome.

BRIEF SUMMARY OF THE INVENTION

The invention provides methods and/or kits for stimulating weight loss, lowering triglyceride and/or lipoprotein levels, and/or treating metabolic syndrome, comprising administering a therapeutically effective amount of DITPA to an individual in need thereof, such as an overweight mammal. In some embodiments, the overweight mammal does not have congestive heart failure.

In one aspect, the invention provides a method for stimulating weight loss in an overweight mammal, comprising administering a therapeutically effective amount of DITPA to the mammal. In another aspect, the invention provides a method for lowering triglyceride levels in an overweight mammal, comprising administering a therapeutically effective amount of DITPA to the mammal. In another aspect, the invention provides a method for lowering lipoprotein levels in an overweight mammal, comprising administering a therapeutically effective amount of DITPA to the mammal. In some embodiments, low density lipoprotein (LDL) levels are decreased. In some embodiments, high density lipoprotein (HDL) levels are decreased. In some embodiments, the mammal has metabolic syndrome. In some embodiments, the mammal is a human. In some embodiments, the human has a body mass index greater than 25. In some embodiments, the human does not have congestive heart failure. In various embodiments, DITPA is administered as a liquid preparation, a solid preparation, a capsule preparation, and an implant preparation. The formulation may also comprise a pharmaceutically acceptable carrier. In some embodiments, the formulation further comprises a stabilizer, an excipient, a solubilizer, an antioxidant, a pain-alleviating agent, and/or an isotonic agent. In various embodiments, DITPA is administered orally, transdermally, by parenteral injection, by parenteral intravenous injection, by implantation, or directly to the pulmonary system of the mammal. In some embodiments, DITPA is administered to the mammal at a dosage of about 0.6 to about 5.1 mg DITPA per kg per day. In some embodiments, DITPA is administered to the mammal at a dosage of about 1.875 to about 3.75 mg per kg per day. In some embodiments, DITPA is administered in combination with a lipid lowering therapeutic agent.

In another aspect of the invention is a method for stimulating weight loss in an overweight mammal, comprising administering to said mammal a therapeutically effective amount of DITPA, wherein the mammal does not have congestive heart failure. In some embodiments, said mammal is a human. In some embodiments, said human has a body mass index over 25. In some embodiments, said mammal has metabolic syndrome. In some embodiments, said DITPA is administered as a formulation selected from the group consisting of: a liquid preparation, a solid preparation, a capsule preparation, and an implant preparation, wherein said formulation further comprises a pharmaceutically acceptable carrier. In some embodiments, said DITPA is administered as a capsule. In some embodiments, said formulation further comprises at least one of a stabilizer, an excipient, a solubilizer, an antioxidant, a pain-alleviating agent, and an isotonic agent. In some embodiments, said DITPA is administered orally, transdermally, by parenteral injection, by parenteral intravenous injection, by implantation, or directly to the pulmonary system of said mammal. In some embodiments, said DITPA is administered orally. In some embodiments, said DITPA is administered to said mammal at a dosage comprising about 0.1 to about 10.0 milligrams per kilogram per day. In some embodiments, said DITPA is administered to said mammal at a dosage comprising about 0.6 to about 5.1 milligrams per kilogram per day. In some embodiments, said DITPA is administered to said mammal at a dosage comprising about 1.875 to about 3.75 milligrams per kilogram per day. In some embodiments, said DITPA is administered to said mammal in combination with a lipid lowering therapeutic agent.

In another aspect of the invention is a method for lowering triglyceride levels in an overweight mammal, comprising administering to said mammal a therapeutically effective amount of DITPA, wherein the mammal does not have congestive heart failure. In some embodiments, said mammal is a human. In some embodiments, said human has a body mass index over 25. In some embodiments, said mammal has metabolic syndrome. In some embodiments, said DITPA is administered as a formulation selected from the group consisting of: a liquid preparation, a solid preparation, a capsule preparation, and an implant preparation, wherein said formulation further comprises a pharmaceutically acceptable carrier. In some embodiments, said DITPA is administered as a capsule. In some embodiments, said formulation further comprises at least one of a stabilizer, an excipient, a solubilizer, an antioxidant, a pain-alleviating agent, and an isotonic agent. In some embodiments, said DITPA is administered orally, transdermally, by parenteral injection, by parenteral intravenous injection, by implantation, or directly to the pulmonary system of said mammal. In some embodiments, said DITPA is administered orally. In some embodiments, said DITPA is administered to said mammal at a dosage comprising about 0.1 to about 10.0 milligrams per kilogram per day. In some embodiments, said DITPA is administered to said mammal at a dosage comprising about 0.6 to about 5.1 milligrams per kilogram per day. In some embodiments, said DITPA is administered to said mammal at a dosage comprising about 1.875 to about 3.75 milligrams per kilogram per day. In some embodiments, said DITPA is administered to said mammal in combination with a lipid lowering therapeutic agent.

In another aspect of the invention is a method for treating metabolic syndrome in an overweight mammal, comprising administering to said mammal a therapeutically effective amount of 3,5-diiodothyropropionic acid ("DITPA"), wherein the mammal does not have congestive heart failure. In some embodiments, said mammal is a human. In some embodiments, said human has a body mass index over 25. In some embodiments, said DITPA is administered as a formulation selected from the group consisting of: a liquid preparation, a solid preparation, a capsule preparation, and an implant preparation, wherein said formulation further comprises a pharmaceutically acceptable carrier. In some embodiments, said DITPA is administered as a capsule. In some embodiments, said formulation further comprises at least one of a stabilizer, an excipient, a solubilizer, an antioxidant, a pain-alleviating agent, and an isotonic agent. In some embodiments, said DITPA is administered orally, transdermally, by parenteral injection, by parenteral intravenous injection, by implantation, or directly to the pulmonary system of said mammal. In some embodiments, said DITPA is administered orally. In some embodiments, said DITPA is administered to said mammal at a dosage comprising about 0.1 to about 10.0 milligrams per kilogram per day. In some embodiments, said DITPA is administered to said mammal at a dosage comprising about 0.6 to about 5.1 milligrams per kilogram per day. In some embodiments, said DITPA is administered to said mammal at a dosage comprising about 1.875 to about 3.75 milligrams per kilogram per day. In some embodiments, said DITPA is administered to said mammal in combination with a lipid lowering therapeutic agent.

In another aspect, the invention provides kits for use in any of the methods described herein, comprising at least one unit dose of DITPA, and optionally comprising instructions for use in methods for stimulating weight loss, lowering triglyceride levels, and/or treating metabolic syndrome.

In another aspect of the invention is provided DITPA for use in a method of treatment comprising stimulating weight loss in an overweight mammal, wherein the overweight mammal does not have congestive heart failure. Further, the DITPA formulations thereof, as described herein, are also intended for use in a method of treatment comprising stimulating weight loss in an overweight mammal, wherein the overweight mammal does not have congestive heart failure, and in accordance with the methods, as described herein, unless clearly dictated otherwise by context or specifically noted.

In another aspect of the invention is provided the use of DITPA in the manufacture of a medicament for use in stimulating weight loss in an overweight mammal, wherein the overweight mammal does not have congestive heart failure. Further, the formulations thereof, as described herein, are also intended for use in the manufacture of a medicament for use in stimulating weight loss in an overweight mammal, wherein the overweight mammal does not have congestive heart failure, and in accordance with the methods, as described herein, unless clearly dictated otherwise by context or specifically noted.

In another aspect of the invention is provided DITPA for use in a method of treatment comprising lowering triglyercide levels in an overweight mammal in need thereof, wherein the overweight mammal does not have congestive heart failure. Further, the DITPA formulations thereof, as described herein, are also intended for use in a method of treatment comprising lowering triglyercide levels in an overweight mammal in need thereof, wherein the overweight mammal does not have congestive heart failure, and in accordance with the methods, as described herein, unless clearly dictated otherwise by context or specifically noted.

In another aspect of the invention is provided the use of DITPA in the manufacture of a medicament for use in lowering triglyceride levels in an overweight mammal in need thereof, wherein the overweight mammal does not have congestive heart failure. Further, the formulations thereof, as described herein, are also intended for use in the manufacture of a medicament for use in lowering triglyceride levels in an overweight mammal in need thereof, wherein the overweight mammal does not have congestive heart failure, and in accordance with the methods, as described herein, unless clearly dictated otherwise by context or specifically noted.

In another aspect of the invention is provided DITPA for use in a method of treatment of metabolic syndrome in an overweight mammal in need thereof, wherein the overweight mammal does not have congestive heart failure. Further, the DITPA formulations thereof, as described herein, are also intended for use in a method of treatment of metabolic syndrome in an overweight mammal in need thereof, wherein the overweight mammal does not have congestive heart failure, and in accordance with the methods, as described herein, unless clearly dictated otherwise by context or specifically noted.

In another aspect of the invention is provided the use of DITPA in the manufacture of a medicament for use in treating metabolic syndrome in an overweight mammal in need thereof, wherein the overweight mammal does not have congestive heart failure. Further, the formulations thereof, as described herein, are also intended for use in the manufacture of a medicament for use in treating metabolic syndrome in an overweight mammal in need thereof, wherein the overweight mammal does not have congestive heart failure, and in accordance with the methods, as described herein, unless clearly dictated otherwise by context or specifically noted.

Unless otherwise noted, the DITPA formulations as described herein are intended for use in the methods of treatment as described herein and may be incorporated in the kits described herein.

DETAILED DESCRIPTION OF THE INVENTION

The invention provides methods, compositions, and kits for stimulating weight loss and/or lowering triglyceride and/or lipoprotein levels using DITPA. In methods of the invention, a therapeutically effective amount of DITPA is administered to an overweight individual to effect weight loss, and/or lowering of triglyceride and/or lipoprotein levels, and/or treatment of metabolic syndrome. In some embodiments, the overweight individual is a mammal that does not have congestive heart failure.

Unless otherwise indicated, the invention is not limited to specific pharmaceutical formulations, formulation components, modes of administration, or the like, as such may vary. It is also to be understood that the terminology used herein is for the purpose of describing particular embodiments only and is not intended to be limiting.

Definitions

As used in the specification and the appended claims, the singular forms "a," "an," and "the" include plural referents unless the context clearly dictates otherwise. Thus, for example, reference to "a pharmaceutically acceptable carrier" includes two or more such carriers as well as a single carrier, and the like.

As used herein, "treatment" or "treating" is defined as therapeutically beneficial administration of a pharmaceutical composition of the present invention to an individual. One outcome of the treatment may be stimulating weight loss of an individual (such as a mammal). Another outcome of the treatment may be lowering triglyceride levels in the body of an individual (such as a mammal). Another outcome of the treatment may be reduction or elimination of one or more symptoms of metabolic syndrome in an individual (such as a mammal), for example, stimulating weight loss, or lowering triglyceride levels.

As used herein, "administration" or "administering" is defined as providing a pharmaceutical composition of the present invention to a mammal (e.g., a human) in need of treatment.

As used herein, "therapeutically effective amount" refers to the amount of DITPA that will render a desired therapeutic outcome (e.g., stimulating weight loss or lowering triglyceride levels). A therapeutically effective amount may be administered in one or more doses. DITPA is generally administered in a pharmaceutically acceptable carrier.

By "pharmaceutically acceptable" is meant a material that is not biologically or otherwise undesirable, i.e., the material may be incorporated into a pharmaceutical composition administered to a patient without causing any significant undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug Administration.

As used herein, the "Body Mass Index (BMI)" is calculated as kilogram of body weight per height in meters squared ($kg/m^2$). Generally, a human with a BMI in the range of 25-30 $kg/m^2$ is considered overweight, with obesity at a BMI greater than 30 $kg/m^2$. A skilled artisan would understand that the BMI-based definition of overweight may be modified to reflect changes in understanding of the condition or practices in the field. Such changes to the BMI-based definition of overweight are contemplated herein. A skilled artisan would also understand that other methods of measurement may be used to define overweight. Such methods are also contemplated in the present invention.

As used herein, the term "overweight" refers to an individual having more body fat than is typical or required for the normal functioning of the body.

As used herein, the term "triglyceride" is defined as a chemical having a structure of: $CH_2COOR$—$CHCOOR'$—$CH_2$—$COOR"$ wherein R, R', and R" are long alkyl chains; wherein the three fatty acids RCOOH, R'COOH and R"COOH can be all different, all the same, or only two the same.

As used herein, the term "metabolic syndrome" is defined as in the Third Report of the National Cholesterol Education Program Expert Panel on Detection, Evaluation and Treatment of High Blood Cholesterol in Adults (ATP-III). E. S. Ford et al., JAMA, vol. 287(3), Jan. 16, 2002, pp 356-359. The metabolic syndrome is characterized by a group of metabolic risk factors, including abdominal obesity, hypertriglyceridemia, low HDL cholesterol, high blood pressure, and high fasting plasma glucose. A human is defined to have metabolic syndrome when the human has 3 or more aforementioned symptoms.

As used herein, the term "congestive heart failure" is defined to mean a syndrome in a mammal due to any structural or functional cardiovascular disorder that impairs the ability of the heart to fill with or pump a sufficient amount of blood throughout the body. This can result from, for example, narrowed arteries that supply blood to the heart muscle (coronary artery disease); past heart attack, or myocardial infarction, with scar tissue that interferes with the heart muscle's normal work; high blood pressure; heart valve disease, due to past rheumatic fever or other causes; primary disease of the heart muscle itself (cardiomyopathy); heart defects present at birth (congenital heart defects); or infection of the heart valves and/or heart muscle itself (endocarditis and/or myocarditis).

Methods of Use

Methods are provided for administration of DITPA to an overweight individual in need of treatment for stimulating weight loss, lowering triglyceride levels, lowering lipoprotein levels, or treating metabolic syndrome. Methods include administration of one or more unit doses of DITPA in a therapeutically effective amount. In methods of the invention, DITPA is generally administered in a pharmaceutically acceptable carrier. In some embodiments, the individual to whom DITPA is administered does not have congestive heart failure. In some embodiments, the individual has a Body Mass Index greater than 25.

A therapeutically effective dose may be administered as a single dose or in multiple doses per day, with the total daily dosage comprising a total dosage of about 0.1 to about 10 milligrams DITPA per kilogram per day. In one embodiment, DITPA is administered at a dosage of about 0.6 to about 5.1 milligrams per kilogram per day. In another embodiment, DITPA is administered at a dosage of about 1.875 to about 3.75 milligrams per kilogram per day.

In various embodiments, methods of the invention comprise administering any of about 0.1, 0.2, 0.3, 0.4, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10.0 milligrams DITPA per kilogram per day. In various embodiments, about 0.1 mg to about 0.2 mg, about 0.2 mg to about 0.5 mg, about 0.5 mg to about 1.0 mg, about 1.0 mg to about 2.0 mg, about 2.0 mg to about 4.0 mg, about 4.0 mg to about 6.0 mg, about 6.0 mg to about 8.0 mg, or about 8.0 mg to about 10.0 mg DITPA is administered per kilogram per day.

In various embodiments, a total dose of any of about 4.5, 10, 20, 30, 45, 50, 75, 90, 125, 150, 180, 200, 225, 250, 270, 300, 325, 360, 400, or 450 mg of DITPA is administered per day. In some embodiments, about 45 mg to about 100 mg, about 100 mg to about 200 mg, about 200 mg to about 300 mg, about 300 mg to about 400 mg, or about 400 mg to about 450 mg DITPA is administered per day.

In some embodiments, a therapeutically effective dosage of DITPA is administered in conjunction with one or more additional therapeutic agents, such as one or more lipid lowering agents, either concurrently or sequentially with respect to administration of DITPA.

In some embodiments, weight loss comprises a reduction of any of about 2% to about 15% body weight, or lowering of Body Mass Index by about 4% to about 12%. In some embodiments, reduction in triglyceride level comprises a reduction of any of about 10, 15, 20, 25, 30, 35, or 40% triglyceride. In some embodiments, treatment of metabolic syndrome comprises amelioration or elimination of one or more symptoms, such as improvement in exercise tolerance or decreased shortness of breath.

DITPA has been previously described, and preparation may be achieved in accordance with methods that are well known in the art. See, e.g., U.S. Pat. No. 6,534,676.

Modes of Administration

Administration of DITPA in accordance with the methods of the invention may be via any route that provides a desired therapeutically effective amount and outcome. Generally, DITPA is administered in a pharmaceutical composition that comprises a unit dose of DITPA and a pharmaceutically acceptable carrier. For example, administration may be oral or parenteral (e.g., intravenous, subcutaneous, intramuscular), transdermal, transmucosal (including buccal, nasal, rectal, sublingual, and vaginal), by inhalation, or via an implanted reservoir in a dosage form.

Depending on the intended mode of administration, the pharmaceutical formulation may be a solid, semi-solid, or liquid, such as, for example, a tablet, a capsule, a caplet, a liquid, a suspension, an emulsion, a gel, a suppository, granules, pellets, beads, a powder, or the like, preferably in unit dosage form suitable for single administration of a precise dosage. Suitable pharmaceutical compositions and dosage forms may be prepared using conventional methods known to those in the field of pharmaceutical formulation and described in the pertinent texts and literature, e.g., in *Remington: The Science and Practice of Pharmacy* (Easton, Pa.: Mack Publishing Co., 1995). For those compounds that are orally active, oral dosage forms are generally preferred, and include tablets, capsules, caplets, solutions, suspensions, and syrups, and may also comprise a plurality of granules, beads, powders, or pellets that may or may not be encapsulated. Preferred oral dosage forms are tablets and capsules.

In some embodiments, DITPA capsules for oral administration comprise about 45 or about 90 mg of DITPA. In one embodiment, the capsules comprise about 45 mg of DITPA, about 149 mg microcrystalline cellulose (e.g., Avicel PH 302), and about 2 mg magnesium stearate. In one embodiment, the capsules comprise about 90 mg of DITPA, about 125 mg microcrystalline cellulose (e.g., Avicel PH 302), and about 4 mg magnesium stearate. In some embodiments, capsules for oral administration comprise about 25 to about 360 mg DITPA. In some embodiments, capsules for oral administration comprise any of about 25, 30, 40, 45, 50, 55, 60, 65, 70, 75, 80, 85, 90, 95, 100, 105, 110, 115, or 120, 125, 150, 175, 200, 225, 250, 275, 300, 325, 350, or 360 mg DITPA.

Tablets may be manufactured using standard tablet processing procedures and equipment. Direct compression and granulation techniques are preferred. In addition to the active agent, tablets will generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose, and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

For manufacturing capsules, the active agent-containing composition may be encapsulated in the form of a liquid or solid (including particulates such as granules, beads, powders, or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, *Remington: The Science and Practice of Pharmacy*, cited supra, which describes materials and methods for preparing encapsulated pharmaceuticals. In one embodiment, DITPA capsules are gelatin capsules containing about 45 milligrams or about 90 milligrams of DITPA, microcrystalline cellulose and magnesium stearate.

Oral dosage forms, whether tablets, capsules, caplets, or particulates, may, if desired, be formulated so as to provide for gradual, sustained release of the active agent over an extended time period. Generally, as will be appreciated by those of ordinary skill in the art, sustained release dosage forms are formulated by dispersing the active agent within a matrix of a gradually hydrolyzable material such as a hydrophilic polymer, or by coating a solid, drug-containing dosage form with such a material. Hydrophilic polymers useful for providing a sustained release coating or matrix include, by way of example: cellulosic polymers such as hydroxypropyl cellulose, hydroxyethyl cellulose, hydroxypropyl methyl cellulose, methyl cellulose, ethyl cellulose, cellulose acetate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate; and vinyl polymers and copolymers such as polyvinyl pyrrolidone, polyvinyl acetate, and ethylene-vinyl acetate copolymer.

Preparations according to this invention for parenteral administration include sterile aqueous and nonaqueous solutions, suspensions, and emulsions. Injectable aqueous solutions contain the active agent in water-soluble form. Examples of nonaqueous solvents or vehicles include fatty oils, such as olive oil and corn oil, synthetic fatty acid esters, such as ethyl oleate or triglycerides, low molecular weight alcohols such as propylene glycol, synthetic hydrophilic polymers such as polyethylene glycol, liposomes, and the like. Parenteral formulations may also contain adjuvants such as solubilizers, preservatives, wetting agents, emulsifiers, dispersants, and stabilizers, and aqueous suspensions may contain substances that increase the viscosity of the suspension, such as sodium carboxymethyl cellulose, sorbitol, and dextran. Injectable formulations are rendered sterile by incorporation of a sterilizing agent, filtration through a bacteria-retaining filter, irradiation, or heat. They can also be manufactured using a sterile injectable medium. The active agent may also be in dried, e.g., lyophilized, form that may be rehydrated with a suitable vehicle immediately prior to administration via injection.

DITPA may also be administered through the skin using conventional transdermal drug delivery systems, wherein the active agent is contained within a laminated structure that serves as a drug delivery device to be affixed to the skin. In such a structure, the drug composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. Transdermal drug delivery systems may in addition contain a skin permeation enhancer.

DITPA may also be administered directly to the pulmonary system of mammals and human, for example, in the form of inhalation or insufflation. For administration by inhalation or insufflation a DITPA solution may be delivered in the form of an aerosol spray presentation from pressurized packs or nebulizer, with the use of suitable propellants such as carbon dioxide or other suitable gasses.

In addition to the formulations described previously, DITPA may also be formulated as a depot preparation for controlled release of the active agent, preferably sustained release over an extended time period. These sustained release dosage forms are generally administered by implantation (e.g., subcutaneously or intramuscularly or by intramuscular injection).

Although the present compositions will generally be administered orally, parenterally, transdermally, directly to the pulmonary system, or via an implanted depot, other modes of administration are suitable as well. For example, administration may be rectal or vaginal, preferably using a suppository that contains, in addition to the active agent, excipients such as a suppository wax. Formulations for nasal or sublingual administration are also prepared with standard excipients well known in the art. The pharmaceutical compositions of the invention may also be formulated for inhalation, e.g., as a solution in saline, as a dry powder, or as an aerosol.

Combination Therapy

In some embodiments of the present invention, DITPA is administered in combination with a single or a plurality of lipid lowering agents. Administration of one or more lipid lowering agents may be either concurrent or sequential with respect to administration of DITPA. For concurrent administration, DITPA and one or more lipid lowering agents may be administered in the same or different formulations. As used herein, the term "lipid lowering agent" is defined as a drug that can be used to lower plasma lipid, e.g., cholesterol, triglyceride, levels and/or raise high-density lipoprotein levels. Examples of such lipid lowering agents include, but are not limited to, HMG CoA reductase inhibitors commonly referred to as "statins," bile acid sequestrants, fibric acid derivatives, nicotinic acid (Niacin™), probucol (Lorelco™), and inhibitors of cholesterol absorption such as ezetimibe (Zetia™). Examples of HMG CoA reductase inhibitors include, but are not limited to, atorvastatin (Lipitor™), simvastatin (Zocor™), fluvastatin (Lescol™), lovastatin (Mevacor™), rosuvastatin (Crestor™), and pravastatin (Pravochol™) or the like. Examples of bile acid sequestrants include, but are not limited to, cholestyramine (Cholybar™, Questran™), and colestipol (Colestid™). Examples of fibric acid derivatives include, but are not limited to, gemfibrozil (Lopid™), clofibrate (Atromid-S™), and fenofibrate (Tricor™). In some embodiments, the lipid lowering agents are co-administered with DITPA. In some embodiments, the lipid lowering agents are administered separately, but within a treatment regime that includes administration of DITPA.

Pharmaceutical Compositions

The invention provides pharmaceutical compositions for use in any of the methods described herein, comprising DITPA as a therapeutically active ingredient. A pharmaceutical compositions for use in the methods of the invention generally comprises a unit dose of DITPA and a pharmaceutically acceptable carrier. In some embodiments of the present invention, a pharmaceutical composition further comprises one or a plurality of second therapeutic ingredients, such as one or a plurality of lipid lowering agents. In some embodiments, the pharmaceutical composition comprises about 25 to about 360 mg of DITPA. In some embodiments, the pharmaceutical composition comprises any of about 25, 30, 40, 45, 50, 55, 60, 65, 70, 75, 80, 85, 90, 95, 100, 105, 110, 115, or 120, 125, 150, 175, 200, 225, 250, 275, 300, 325, 350, or 360 mg of DITPA.

Kits

Kits are provided for use in methods of the invention for stimulating weight loss, lowering triglyceride levels, or treatment of metabolic syndrome. The kits include a pharmaceutical composition for use in a method of the invention, for example, including at least one unit dose of DITPA, and instructions providing information to a health care provider or patient regarding such usage. Instructions may be provided in printed form or in the form of an electronic medium such as a floppy disc, CD, or DVD, or in the form of a website address where such instructions may be obtained.

Suitable packaging is provided. As used herein, "packaging" refers to a solid matrix or material customarily used in a system and capable of holding within fixed limits a DITPA-containing composition suitable for administration to an individual. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

In some embodiments, such kits can contain dosage forms, e.g., separately sealed, and/or individually removable unit dosage forms packaged in a container, wherein each unit dosage form comprises a pharmaceutical composition containing (i) a unit dosage of a DITPA-containing composition as described herein, and (ii) a pharmaceutically acceptable carrier, wherein the unit dosage is effective to provide a therapeutically effective amount. Kits may further comprise instructions describing administration of the dosage forms in a manner effective to stimulate weight loss, to lower triglyceride levels, and/or to treat metabolic syndrome.

In some embodiments, the DITPA-containing composition in the kit is in an orally active form, the pharmaceutically acceptable carrier is suitable for oral drug delivery, and the instructions describe oral administration of the dosage forms in a manner effective to treat stimulate weight loss, to lower triglyceride levels, and/or to treat metabolic syndrome. In some embodiments in which DITPA is administered parenterally, kits may also optionally include equipment for administration of DITPA, such as, for example, syringes or equipment for intravenous administration, and/or a sterile solution, e.g., a diluent such as 5% dextrose, for preparing a dry powder (e.g., lyophilized) composition for administration.

Kits of the invention may include, in addition to DITPA, one or a plurality of second therapeutic ingredients, such as one or a plurality of lipid lowering agents, for use with DITPA as described in the methods above.

The following examples are intended to illustrate but not limit the invention.

EXAMPLES

Example 1

Human Clinical Study with DITPA

Fifty-four patients with a history of congestive heart failure were administered DITPA or placebo in a 2:1 randomized and double-blinded manner for a maximum of 26 weeks. Sixteen out of the 54 patients had a body mass index lower than or equal to 25. The other 38 patients, who were overweight, had a body mass index greater than 25. The patients in the study were administered DITPA orally twice per and the dose began at 90 mg/day and increased to 180 mg/day after two weeks. In half of the DITPA patients, the dose was increased further to 270 mg/day after two weeks, and then to 360 mg/day. Patients were randomized 1:1:1 to DITPA 180 mg/day, DITPA 360 mg/day, or placebo.

Results

In 16 patients with a body mass index greater than 25, 71.05% experienced a weight loss of 2% or more. In 38 patients with a body mass index less than or equal to 25, 37.5% experienced a weight loss of 2% or more. Thus, more than two-thirds of patients with a body mass index greater than 25 lost weight, and over one-third of patients with a body mass index less than or equal to 25 experienced a weight loss of 2% or more.

The results of this study show that administration of DITPA caused a greater decrease in weight in overweight patients than those of normal body weight. However, some patients who were not overweight (i.e., body mass index less than or equal to 25) also experienced weight loss.

Example 2

A Randomized, Double-Blind, Placebo-Controlled Study of DITPA for the Reduction of Weight and Improvement in Metabolic Abnormalities in Obese Adults Receiving Dietary Counseling Objectives The objectives of this study are to evaluate the efficacy of DITPA in addition to a hypocaloric diet for weight reduction in obese adult humans. Secondary objectives are to evaluate the effects of DITPA on serum triglycerides, LDL cholesterol, waist circumference, fat free mass, resting energy expenditure, markers of insulin sensitivity and bone turnover, and to evaluate the safety of DITPA in this patient population.

Study Design

This is a single-center, randomized, double-blind, placebo-controlled study to evaluate the effect of DITPA on weight reduction and dyslipidemia in obese patients who are receiving dietary counseling regarding a hypocaloric diet.

Patients are randomized to 1 of 3 treatment groups in a 1:1:1 ratio:

DITPA 45 mg BID taken orally
DITPA 90 once daily taken orally
Placebo BID taken orally Those patients randomized to receive DITPA at 90 mg/day receive 45 mg/day for the first 2 weeks, followed by 90 mg/day (90 mg qd or 45 mg bid) for 14 weeks.

Study Duration and Number of Visits

The study consists of a Screening Phase, a Pre-Randomization Phase that consists of dietary counseling plus a 2-week Placebo Run-In Period, and a 16-week Treatment Phase. Patients are seen 28 days after the End of Treatment Visit. The total duration on study is approximately 24 weeks.

Study Population

The study population consists of patients with a BMI>30 kg/m$^2$ who are interested in weight loss. In order to evaluate the potential effect of DITPA on serum triglycerides, at least 50% of the targeted study population has hypertriglyceridemia (>150 mg/dL). The study population does not include patients with congestive heart failure.

Endpoints

The primary endpoint is weight change from baseline to week 16.

Secondary endpoints include: percent change in weight from baseline to week 16; proportion of subjects achieving weight loss greater than or equal to 5%; proportion of subjects achieving weight loss greater than or equal to 10%; percent change in serum triglyceride levels from baseline to week 16; percent change in total cholesterol levels from baseline to week 16; percent change in LDL cholesterol levels from baseline to week 16; change in waist circumference from baseline to week 16; change in fat mass by dual energy X-ray absorptiometry (DXA) from baseline to week 16; change in fat free mass by DXA from baseline to week 16; change in percentage of body fat by DXA from baseline to week 16; change in resting energy expenditure from baseline to week 16; change in nocturnal heart rate from baseline to week 16; change in QUICKI index $[1/\log_{10}(\text{insulin})+\log_{10}(\text{glucose})]$ from baseline to week 12; and change in markers of bone formation and bone resorption from baseline to week 12.

Differences in weight change from baseline between the placebo group and the two treatment groups are determined by analysis of variance (ANOVA). The null hypothesis is that the average weight change over the study interval does not differ between the three groups. If the F statistic for the ANOVA is significant, pair-wise comparisons are made using t-tests to determine which groups are different. No correction is made for multiple comparisons, the alpha level is set at 0.05, and all tests are two-sided. Analyses are intention to treat. Between-group differences in the change in other continuous secondary variables are also assessed with ANOVA. For categorical variables (e.g., percent with 5% weight loss), logistic regression analysis with treatment group is the primary exposure variable.

All publications, patents, and patent applications cited herein are hereby incorporated by reference in their entireties for all purposes and to the same extent as if each individual publication, patent, or patent application were specifically and individually indicated to be so incorporated by reference.

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention, which is delineated by the appended claims. While the invention has been exemplified with respect to treating humans, the invention also advantageously may be used for treating overweight animals such as dogs and cats, and other domesticated animals. Also, while administration of DITPA reduces triglycerides in overweight individuals, individuals of normal weight also may benefit by a reduction of triglycerides from administration of DITPA in accordance with the present invention.

We claim:

1. A method for stimulating weight loss in an overweight mammal, comprising administering to said mammal a therapeutically effective amount of 3,5-diiodothyropropionic acid ("DITPA"), wherein said mammal does not have congestive heart failure.

2. The method of claim 1, wherein said mammal is a human.

3. The method of claim 2, wherein said human has a body mass index over 25.

4. The method of claim 1, wherein said DITPA is administered as a formulation selected from the group consisting of: a liquid preparation, a solid preparation, a capsule preparation, and an implant preparation, wherein said formulation further comprises a pharmaceutically acceptable carrier.

5. The method of claim 1, wherein said DITPA is administered as a capsule.

6. The method of claim 4, wherein said formulation further comprises at least one of a stabilizer, an excipient, a solubilizer, an antioxidant, a pain-alleviating agent, and an isotonic agent.

7. The method of claim 1, wherein said DITPA is administered orally, transdermally, by parenteral injection, by parenteral intravenous injection, by implantation, or directly to the pulmonary system of said mammal.

8. The method of claim 1, wherein said DITPA is administered orally.

9. The method of claim 1, wherein said DITPA is administered to said mammal at a dosage comprising about 0.1 to about 10.0 milligrams per kilogram per day.

10. The method of claim 9, wherein said DITPA is administered to said mammal at a dosage comprising about 0.6 to about 5.1 milligrams per kilogram per day.

11. The method of claim 10, wherein said DITPA is administered to said mammal at a dosage comprising about 1.875 to about 3.75 milligrams per kilogram per day.

12. The method of claim 1, wherein said DITPA is administered to said mammal in combination with a lipid lowering therapeutic agent.

13. A method for lowering triglyceride levels in an overweight mammal, comprising administering to said mammal a therapeutically effective amount of 3,5-diiodothyropropionic acid ("DITPA"), wherein said mammal does not have congestive heart failure.

14. The method of claim 13, wherein said mammal is a human.

15. The method of claim 14, wherein said human has a body mass index over 25.

16. The method of claim 13, wherein said DITPA is administered as a formulation selected from a group consisting of: a liquid preparation, a solid preparation, a capsule preparation, and an implant preparation, wherein said formulation further comprises a pharmaceutically acceptable carrier.

17. The method of claim 16, wherein said formulation further comprises at least one of a stabilizer, an excipient, a solubilizer, an antioxidant, a pain-alleviating agent, and an isotonic agent.

18. The method of claim 13, wherein said DITPA is administered as a capsule.

19. The method of claim 13, wherein said DITPA is administered orally, transdermally, by parenteral injection, by parenteral intravenous injection, by implantation, or directly to the pulmonary system of said mammal.

20. The method of claim 13, wherein said DITPA is administered orally.

21. The method of claim 13, wherein said DITPA is administered to said mammal at a dosage comprising about 0.1 to about 10.0 milligrams per kilogram per day.

22. The method of claim 21, wherein said DITPA is administered to said mammal at a dosage comprising about 0.6 to about 5.1 milligrams per kilogram per day.

23. The method of claim 22, said DITPA is administered to said mammal at a dosage comprising about 1.875 to about 3.75 milligrams per kilogram per day.

24. The method of claim 13, wherein said DITPA is administered to said mammal in combination with a lipid lowering therapeutic agent.

25. A kit comprising:
at least one unit dose of 3,5-diiodothyroproprionic acid ("DITPA"), and instructions for use in the method according to claim 13.

26. A kit comprising:
(a) at least one unit dose of 3,5-diiodothyropropionic acid ("DITPA"), and
(b) instructions for use in the method according to claim 1.

* * * * *